United States Patent [19]
Fryer et al.

[11] Patent Number: 6,147,502
[45] Date of Patent: Nov. 14, 2000

[54] METHOD AND APPARATUS FOR MEASURING BUTTERFAT AND PROTEIN CONTENT USING MICROWAVE ABSORPTION TECHNIQUES

[75] Inventors: Michael O. Fryer, Roberts, Id.; Andrea J. Hills, Iowa City, Iowa; John L. Morrison, Idaho Falls, Id.

[73] Assignee: Bechtel BWXT Idaho, LLC, Idaho Falls, Id.

[21] Appl. No.: 09/058,265

[22] Filed: Apr. 10, 1998

[51] Int. Cl.$^7$ ................................................ G01R 27/04
[52] U.S. Cl. ........................ 324/637; 324/636; 324/637; 324/638; 324/642; 324/646; 73/53.02; 73/61.72
[58] Field of Search ..................... 324/600, 637, 324/636, 638, 646, 647, 652; 73/53.02, 61.42, 61.43, 61.71; 250/336.1; 426/99, 231; 333/135, 230, 227

[56] References Cited

U.S. PATENT DOCUMENTS

| | | | |
|---|---|---|---|
| 3,090,018 | 5/1963 | Foss | 333/227 |
| 3,161,768 | 12/1964 | Goulden | 250/339.01 |
| 3,458,808 | 7/1969 | Agdur | 324/633 |
| 3,492,601 | 1/1970 | Omori | 333/1.1 |
| 4,145,450 | 3/1979 | Winder et al. | 426/231 |
| 4,247,773 | 1/1981 | Nexo et al. | 250/339 |
| 4,310,763 | 1/1982 | Shields | 250/339 |
| 4,359,638 | 11/1982 | Allport | 378/50 |
| 4,447,725 | 5/1984 | Biggs et al. | 250/339 |
| 4,458,217 | 7/1984 | Wong et al. | 333/26 |
| 4,663,530 | 5/1987 | Shields | 250/339 |
| 4,855,601 | 8/1989 | Savoyet | 250/339 |
| 5,343,044 | 8/1994 | Sjaunja et al. | 250/339.09 |
| 5,550,432 | 8/1996 | Barker | 315/5 |
| 5,644,244 | 7/1997 | Marrelli et al. | 324/637 |
| 5,712,605 | 1/1998 | Flory et al. | 333/219 |
| 5,923,174 | 7/1999 | Darling, Jr. | 324/637 |

*Primary Examiner*—Josie Ballato
*Assistant Examiner*—A Deb
*Attorney, Agent, or Firm*—Workman Nydegger & Seeley

[57] ABSTRACT

A self calibrating method and apparatus for measuring butterfat and protein content based on measuring the microwave absorption of a sample of milk at several microwave frequencies. A microwave energy source injects microwave energy into the resonant cavity for absorption and reflection by the sample undergoing evaluation. A sample tube is centrally located in the resonant cavity passing therethrough and exposing the sample to the microwave energy. A portion of the energy is absorbed by the sample while another portion of the microwave energy is reflected back to an evaluation device such as a network analyzer. The frequency at which the reflected radiation is at a minimum within the cavity is combined with the scatter coefficient $S_{11}$ as well as a phase change to calculate the butterfat content in the sample. The protein located within the sample may also be calculated in a likewise manner using the frequency, $S_{11}$ and phase variables. A differential technique using a second resonant cavity containing a reference standard as a sample will normalize the measurements from the unknown sample and thus be self-calibrating. A shuttered mechanism will switch the microwave excitation between the unknown and the reference cavities. An integrated apparatus for measuring the butterfat content in milk using microwave absorption techniques is also presented.

20 Claims, 5 Drawing Sheets

METHOD AND APPARATUS FOR MEASURING BUTTERFAT AND PROTEIN CONTENT USING MICROWAVE ABSORPTION TECHNIQUES

CONTRACTUAL ORIGIN OF THE INVENTION

The United States has rights in this invention pursuant to Contract No. DE-AC07-94ID13223 between the U.S. Department of Energy and Lockheed Martin Idaho Technologies Company.

BACKGROUND OF THE INVENTION

1. Field of the Invention

This invention generally relates to methods for analyzing milk samples. More specifically, this invention relates to a method and apparatus for calculating the butterfat content in flowing milk.

2. Present State of the Art

For a considerable number of years, farmers have attempted to estimate the quality of the products they produce whether it be grain, potatoes, milk, or livestock. By identifying the best products, they can achieve a higher yield from their efforts, and therefore maximize their profits and minimize waste. To facilitate maximization, farmers may resort to outside experts who will test their products and provide advice based on the test results. For example, in the milk production industry, a dairymen relies on an inspector who travels to their dairy, takes samples from each cow and then returns to a laboratory to test the milk sample for butterfat, protein, lactose, casein or other non-fat solids. There is a lag time of a few days between the removal of a sample from the dairy and the determination of milk component percentages. A better alternative is to have an on-line analyzer which is capable of giving accurate milk component percentages within a short period of time.

Current instrumentation for analyzing milk content does not allow for on-line analysis of milk and, furthermore, employ infrared (IR) technology which has a number of drawbacks. In the prior art approaches, IR radiation is directed at a milk sample and the associated absorption pattern is used to determine the components of the milk. These infrared analyzers require frequent calibration to retain specificity in analysis, especially when calculating a percentage quantity of more complex proteins, like casein. Infrared technology is also commonly employed for evaluation in batch operations, not for in-line analysis.

While the use of infrared techniques in evaluating the butterfat content and other protein contents of milk products is well known, infrared techniques suffer from other short comings including the necessity for frequent calibration of the infrared devices. Furthermore, infrared evaluation devices also require frequent maintenance of the apparatus to maintain adequate optical conditions for testing the milk product. These and other short comings of the infrared and optical systems render them very impractical for use in on-line analysis of butterfat and protein contents as well as for use in an integrated in-line solution for milk product characterization.

Thus, what is needed is a method and apparatus for measuring butterfat content in milk in a near real-time environment capable of processing a substantially larger number of samples of milk products. Furthermore, what is needed is a method and apparatus for evaluating the butterfat content and alternatively protein content in milk products in a timely and in-line manner wherein the evaluation of the characteristics of the milk under test may be performed on a stream of milk rather than in a batch mode process.

SUMMARY AND OBJECTS OF THE INVENTION

It is an object of the present invention to provide a method for measuring butterfat content in milk using microwave absorption measurement techniques for evaluating the milk as it passes through a resonant cavity.

Another object of the present invention is to provide a method for measuring the protein content in milk using microwave absorption measurement techniques as the milk sample passes through a resonant cavity.

Additional objects and advantages of the present invention will be set forth in the description which follows, and in part will be obvious from the description, or may be learned by the practice of the invention. The objects and advantages of the invention may be realized and obtained by means of the instruments and combinations particularly pointed out in the appended claims. To achieve the objects, and in accordance with the invention as embodied and broadly described herein, a method and system capable of measuring butterfat and alternatively protein content in milk using microwave absorption measurement techniques for evaluating the milk sample as it passes through a microwave resonant cavity is provided.

The present invention is based on measuring the magnitude of the scattering parameters (S-parameters) which are characteristic of a microwave transfer function. In particular, the present invention utilizes an indication of the magnitude of the $S_{11}$ reflection parameter which is an indication of the reflected microwave energy as a function of the input microwave energy.

In the present invention, a microwave resonant cavity is coupled to a microwave radiator for propagating microwave energy into the resonant cavity. The microwave cavity is further coupled to an analyzer capable of evaluating the amount of energy absorbed within the cavity by evaluating the amount of energy reflected from the cavity. A sample of milk undergoing a butterfat test, and optionally a protein test, traverses the resonant cavity and is located such that the E-field is maximized and is aligned along the axis of the sample tube presenting the milk sample to the resonant cavity. Microwave energy is thereafter injected into the resonant cavity wherein a portion of the energy is absorbed by the sample with another portion reflected back for evaluation to an analyzer such as a network analyzer. The $S_{11}$ spectra for a given butterfat content is unique and varies with the amount of butterfat inherent in the milk sample. Calculation of the precise butterfat content may be performed using interpolation, such as linear or multi-dimensional interpolation, or even though the use of a neural network technique to determine the sample butterfat values at concentrations other than the empirical calibrated values.

In a yet additional embodiment of the present invention, the milk sample may be in the form of a continuous sample stream or flow of milk, thereby facilitating the continuous monitoring of the butterfat content in a milk stream. By utilizing a resonant cavity approach to evaluate a milk sample, a more simplified and accurate approach to identify butterfat content is developed.

In yet another embodiment of the present invention, the microwave resonant cavity is implemented as a differential cavity wherein one branch of the cavity may contain a reference sample for calibrating the resonant cavity and a second branch may contain the unknown sample to be tested. A shutter mechanism may be employed to alternate and route the microwave energy between the two branches of the differential resonant cavity. Furthermore, the present invention may be yet embodied in a more integrated device wherein a phase lock loop tracks the desired frequencies of the cavity for use in determining the butterfat and alternatively the protein content.

These and other objects and features of the present invention will become more fully apparent from the following description and dependent claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention embodies within its scope both a method and apparatus for measuring the butterfat content, and alternatively the protein content, in milk using microwave absorption techniques. The purpose of the present invention is to provide a means and method for accurately and efficiently calculating the butterfat and protein contents in milk through the use of a device capable of evaluating large volumes of milk and requiring minimal maintenance to the measurement device while performing an evaluation of readily ascertainable parameters. The present invention employs a resonant cavity design capable of facilitating an evaluation of milk in a continuous flow arrangement passing therethrough.

Figure 1:
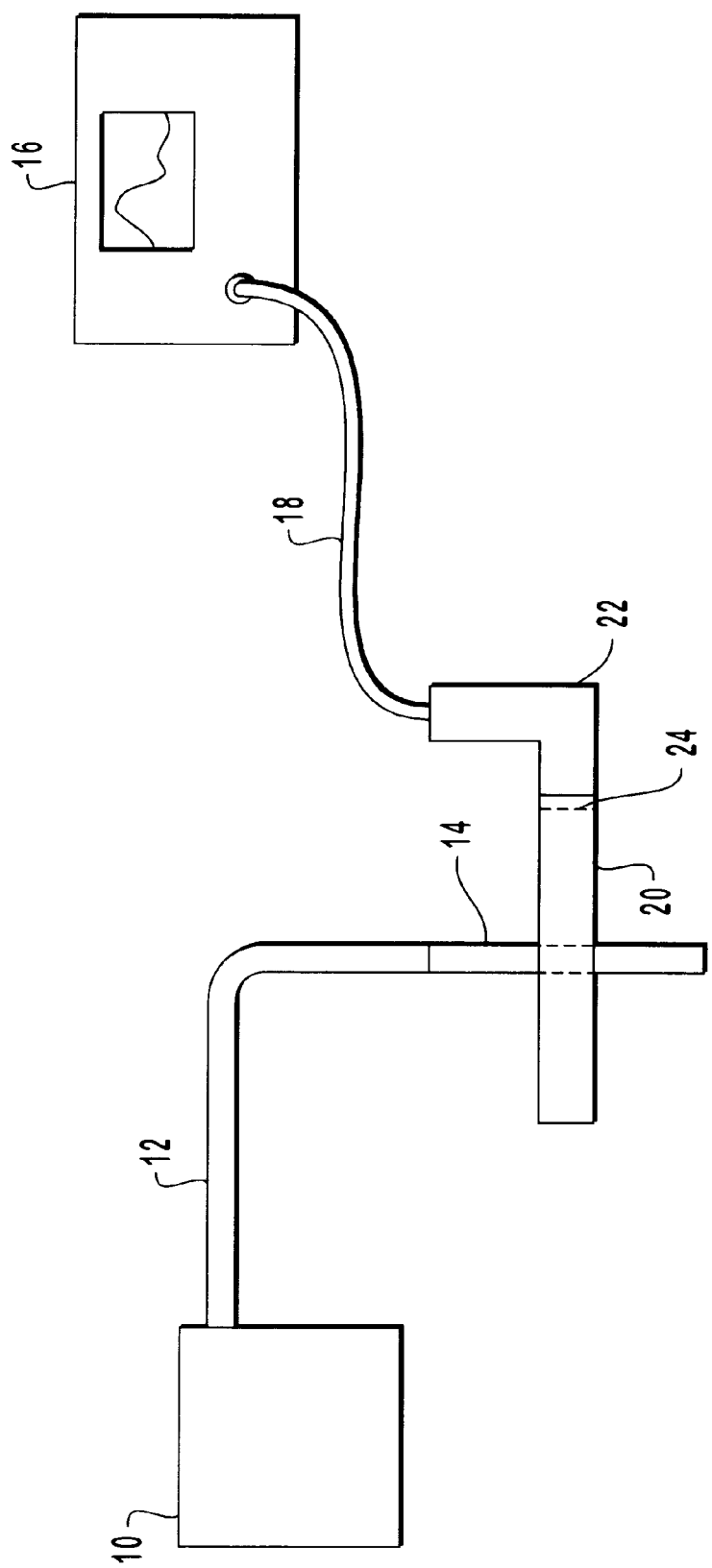
FIG. 1 is a simplified block diagram of an apparatus for evaluating the butterfat and alternatively the protein content of milk through the use of a microwave resonant cavity, in accordance with the preferred embodiment of the present invention.

FIG. 1 is a simplified block diagram of an apparatus for measuring butterfat content, and alternatively protein content, of a milk sample using microwave absorption measurement techniques, in accordance with a preferred embodiment of the present invention. In FIG. 1, a supply of milk is provided such that a sample may be drawn for evaluation of its inherent characteristic content. A sample of milk undergoing diagnosis may be provided in a discrete sample or through the use of a continuous flow sample undergoing periodic or intermittent evaluation. In FIG. 1, a sample for evaluation is provided in a sample tube or other conduit such as depicted by glass or flow tube 14. Alternatively, glass tube 14 may be connected with a continuous flow conduit 12 for receiving a continuous stream of samples as provided from a reservoir 10. Alternatively, reservoir 10 may yet be incorporated enabling retrieval of the milk samples directly from a source such as in the case of providing in-line monitoring at the point of milk collection. Such a monitoring technique provides a method for evaluating individual milk providers to determine the relative quality of each contributing entity.

The present invention employs microwave resonant techniques for evaluating the milk sample to determine its relative qualities. The preferred embodiment employs a microwave energy source to provide the required microwave signals to the milk sample undergoing evaluation. In FIG. 1, the microwave energy source is depicted as a network analyzer 16 capable of generating the aforementioned microwave signals. The microwave signals are routed via a coax cable 18 to a coupler 22 which includes a radiator (not shown) for radiating the microwave's energy upon the milk sample undergoing a testing process. In the present invention, favorable test results were obtained by maintaining the milk sample at a very uniform or consistent temperature throughout the testing process. For the favorable results in the present invention, a constant temperature of about 165° F. to 169° F. was maintained.

In order to generate the appropriate necessary transfer function, a resonant cavity 20 couples or operably interfaces with coupler 22 via an iris 24 to provide the appropriate cavity in which the microwave energy may resonate. Resonant cavity 20 is implemented as a hollow conducting enclosure for containing the electromagnetic energy or microwave energy therein. In the preferred embodiment of the present invention, resonant cavity 20 is implemented as a rectangular resonant cavity having an aperture centrally located through which sample tube 14 may pass. Those skilled in the art appreciate that other iris implementations are equally feasible.

Figure 2B:
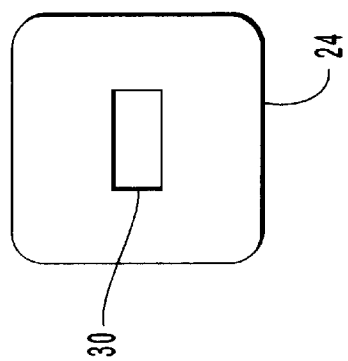
FIG. 2B depicts a schematic of the iris used in conjunction with the resonant cavity.
Figure 2A:
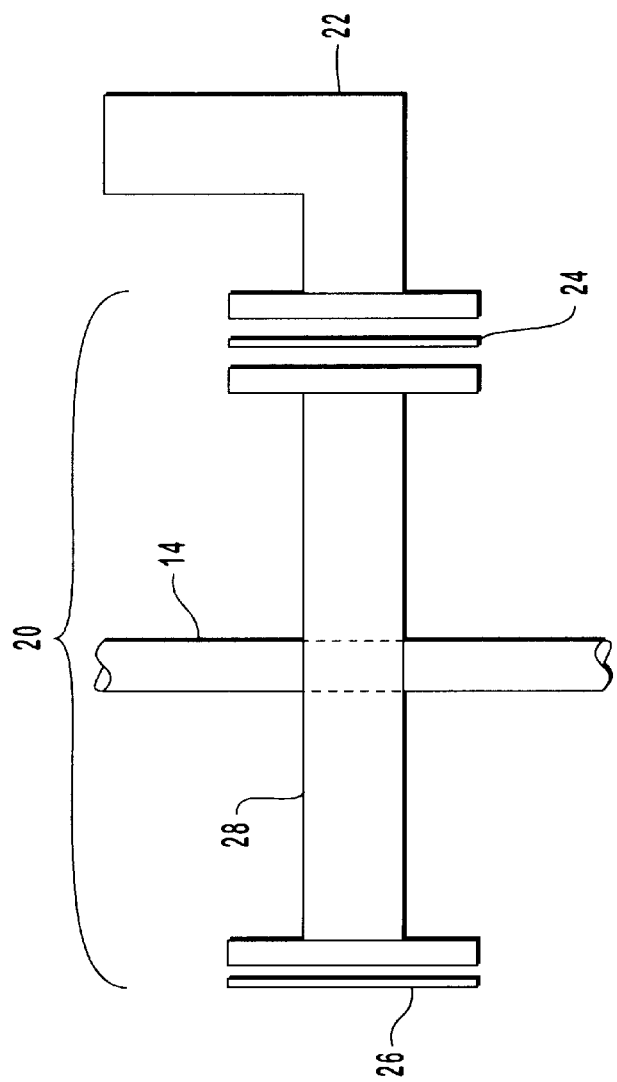
FIG. 2A depicts a schematic of the resonant cavity used in evaluating the butterfat and protein content of a milk sample, in accordance with the preferred embodiment of the present invention.

FIG. 2A is a schematic of a resonant cavity used for measuring the butterfat content in milk, in accordance with a preferred embodiment of the present invention. Resonant cavity 20 is comprised of a metallic channel 28 capable of having a short or an end plate 26 affixed therewith, also consisting of a metallic substance. The other end of metallic channel 28 is interfaced with an iris 24. As indicated in FIG. 2B, iris 24 includes an aperture 30 through which microwave energy may enter into resonant cavity 20. In the preferred embodiment, metallic channel 28 is of a length so as to accommodate the use of microwave frequencies occurring in the X-band. While other bands may also be employed, the present embodiment utilizes the X-band for obtaining favorable results. Those skilled in the art of microwave theory, appreciate that the dimensions for such a frequency band result in the length of metallic chamber 28 being approximately 3 inches in length for covering the 8.2 GHz–12.4 GHz frequency band. Other dimensions of the metallic chamber 28 include a width of approximately 1 inch and a height of approximately ⅜ of an inch. While the preferred embodiment of the present invention employs a rectangular aperture 30, other aperture geometries are also useful for defining the dimensions of resonant cavity 20 and providing an aperture through which microwave energy may enter into resonant cavity 20 and be reflected back therefrom for evaluation.

Contemporaneous with the exposure of the milk sample to the microwave energy, an analyzing device such as a network analyzer 16 (FIG. 1) is used to find the microwave absorption which can be expressed in terms of S-parameters as $1-(S_{11})^2-(S_{21})^2$.

Figure 3:
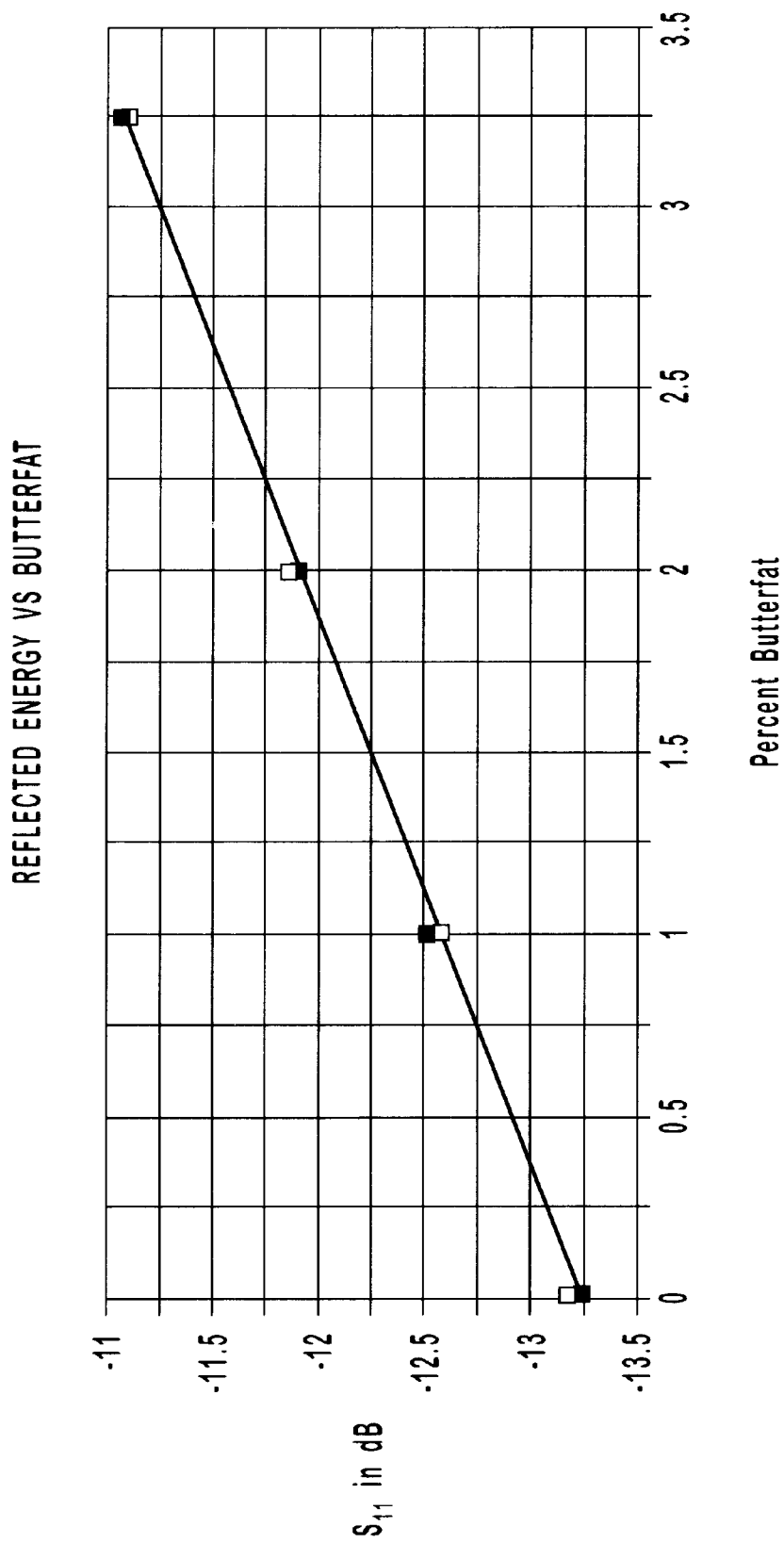
FIG. 3 is a graph of the reflected energy and the corresponding butterfat content derived from empirical testing, in accordance with the preferred embodiment of the present invention.

FIG. 3 is a graph of the percent of butterfat in a milk sample as a function of the reflected energy measured as $S_{11}$ in decibels. In the plot in the present figure, actual milk samples were tested using testing techniques established in the industry to create empirical reference points for known characteristic contents. The results of the correlated evaluation are listed in Table 1.

TABLE 1

| BUTTERFAT MEASURED | PROTEIN MEASURED | AVERAGE $S_{11}$ (dB) | AVERAGE FREQUENCY (GHz) |
| --- | --- | --- | --- |
| 3.37 | 3.29 | −10.483 | 7.8788 |
| 3.28 | 4.81 | −9.719 | 7.8801 |
| 3.21 | 6.39 | −8.902 | 7.8820 |
| 0.91 | 3.33 | −12.224 | 7.8732 |
| 0.87 | 4.76 | −11.120 | 7.8746 |
| 0.80 | 6.18 | −10.192 | 7.8765 |

Using the least squares fit of the butterfat and protein verses the $S_{11}$ and frequency entries, the following results illustrated in Table 2 were obtained.

TABLE 2

| BUTTERFAT MEASURED | BUTTERFAT CURVE FIT | PROTEIN MEASURED | PROTEIN CURVE FIT |
| --- | --- | --- | --- |
| 3.37 | 3.37 | 3.29 | 3.30 |
| 3.28 | 3.29 | 4.81 | 4.80 |
| 3.21 | 3.21 | 6.39 | 6.39 |
| 0.91 | 0.92 | 3.33 | 3.31 |
| 0.87 | 0.86 | 4.76 | 4.83 |
| 0.80 | 0.81 | 6.18 | 6.14 |

Therefore, $S_{11}$ and the frequency of the minimum reflected energy can quite accurately predict both butterfat content and protein content. In the present evaluation, the protein undergoing evaluation is more specifically whey protein.

Figure 4:
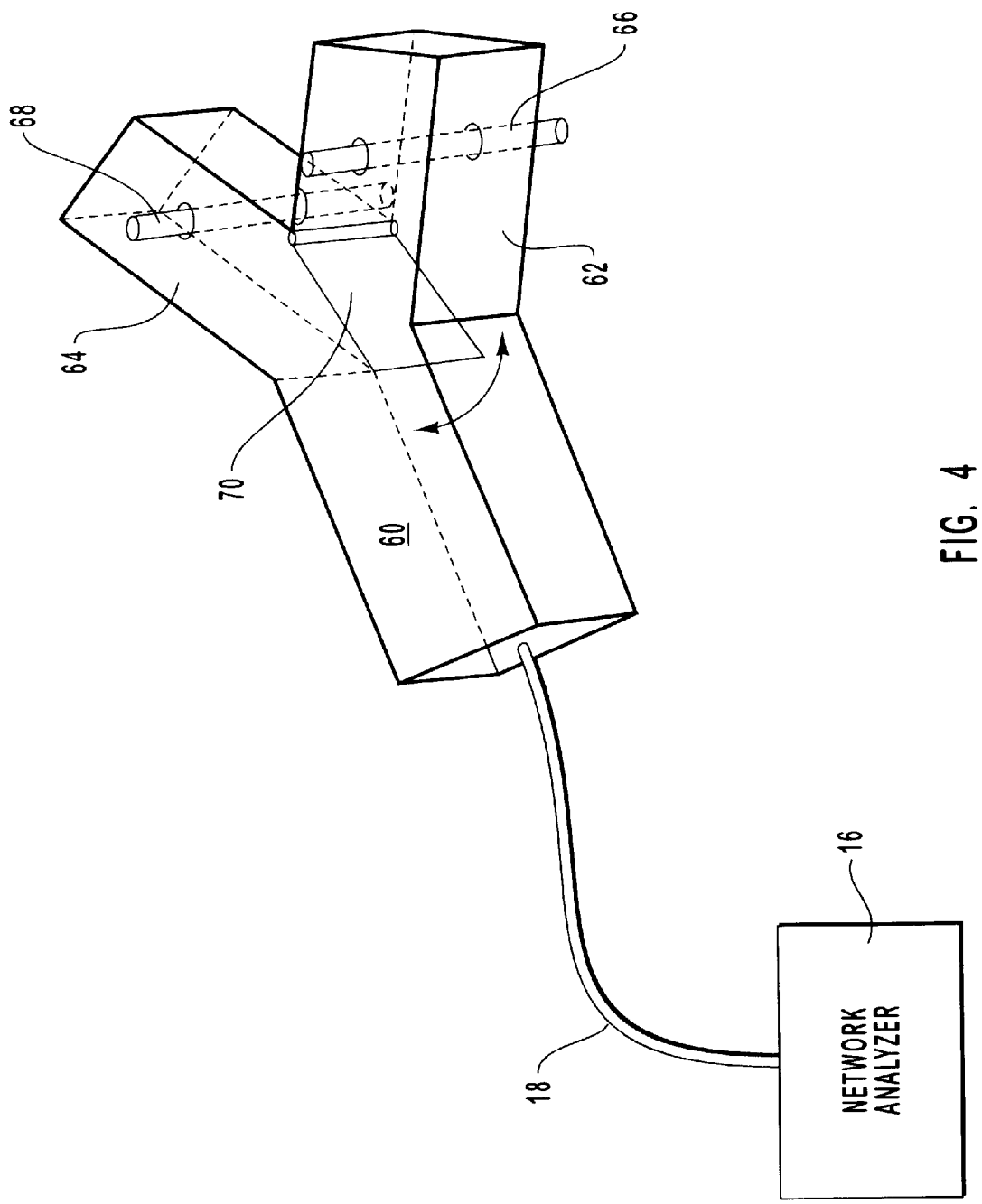
FIG. 4 is a simplified schematic of a differential resonant cavity, in accordance with an alternate embodiment of the present invention.

FIG. 4 depicts a microwave differential resonant cavity for measuring the butterfat content in milk using microwave absorption measurement techniques, in accordance with an alternate embodiment of the present invention. A resonant cavity 60 receives microwave energy from a source such as a network analyzer 16 via a coax cable 18 for excitation within resonant cavity 60. Resonant cavity 60 is configured in a Y-configuration comprised of a first fork 62 wherein the unknown sample such as the milk sample undergoing test is located as depicted as unknown sample 66. Additionally, resonant cavity 60 further comprises a second fork 64 wherein a reference sample 68 may be located containing a known substance or liquid, such as water. The use of a resonant cavity with a small volume of test material located inside one fork accommodates the evaluation of the unknown or test sample using differential techniques. To facilitate the individual measuring of the reflection energy from each of the individual branches of the resonant cavity, resonant cavity 60 further comprises a shutter which may be activated in the resonant cavity for reflecting or routing the microwave energy between a first and second fork. Shutter 70 alternately blocks one of the branches of the Y-configuration and may be activated in a time multiplexed manner enabling time multiplexed measurements of the $S_{11}$ response of each branch or fork. The resultant data may be easily processed such that the unknown sample, such as the milk sample under test, may be differenced or normalized relative to the reference sample. Such a technique facilitates the compensation of undesirable sensitivity such as drifts in electronics, drifts or variations in temperatures of the unknown sample as well as other test condition differences that may exist. Such a technique enables the isolation and measurement of only those sensitivities of the unknown sample relative to the reference sample.

Figure 5:
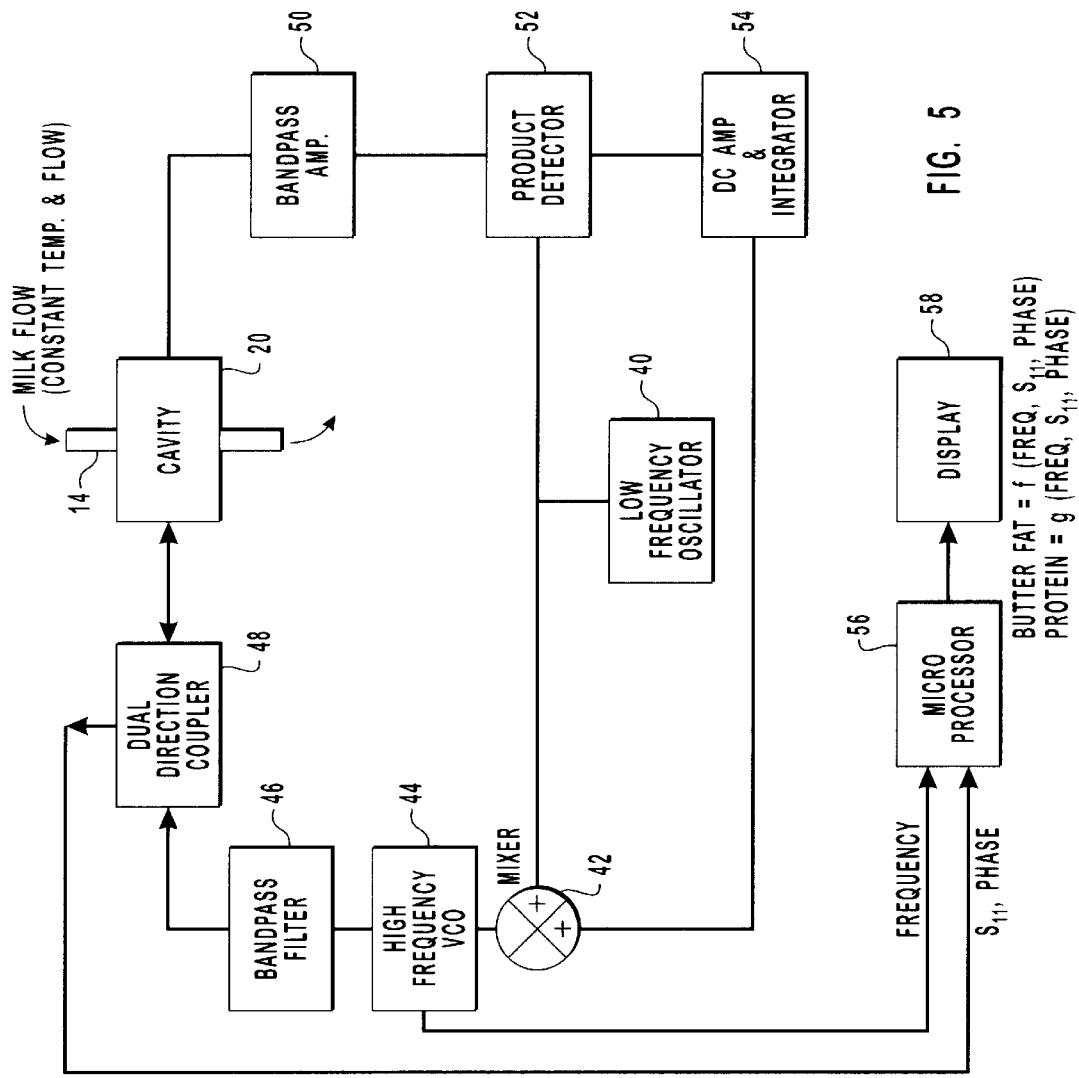
FIG. 5 is a simplified block diagram of an integrated apparatus for evaluating the butterfat and protein contents in a milk sample, in accordance with an embodiment of the present invention.

FIG. 5 is a simplified block diagram of a schematic of a microwave circuit as implemented in an integrated environment, in accordance with a preferred embodiment of the present invention. The integrated apparatus of FIG. 6 incorporates a resonant cavity 20 and sample tube 14 as described above. The present integrated version further incorporates a phase lock loop for generating the frequencies used in the resonant cavity. In the integrated version, rather than incorporating a test equipment type network analyzer, the present embodiment incorporates a simplified phase lock loop design implemented using elements 40 through 54 to generate the microwave energy and perform that portion of the function previously performed by network analyzer 16 (FIG. 1). That is to say, the phase locked loop implementation evaluates and finds the correct frequency to maximize $S_{11}$.

In order to evaluate the reflected coefficient and thereby calculate the butterfat, and alternatively the protein contents, of the sample milk, a dual directional coupler 48 presents the reflected portion of the microwave energy to a microprocessor 56 for analog to digital conversion and evaluation of the $S_{11}$ and phase parameters. The frequency parameter is provided to microprocessor 56 from evaluation of the setting of high frequency voltage control oscillator 44 as utilized in the phase locked loop. Microprocessor 56 further performs the steps of converting the frequency, $S_{11}$ and phase values to the corresponding butterfat and protein values. A display 58 receives the calculated butterfat and alternatively protein calculations from microprocessor 56 for presentation to a user.

While a method and apparatus for measuring butterfat and optionally protein content in milk using microwave absorption techniques as been presented, the present invention may be embodied in other specific forms without departing from the spirit or essential characteristics. The described embodiments are to be considered in all respects as only illustrative and not restrictive. The scope of the invention is, therefore, indicated by the appended claims rather than by the foregoing description. All changes which come within the meaning and range of equivalency of the claims are to be embraced within their scope.

We claim:

1. A method of measuring butterfat content in milk using microwave absorption measurement techniques, comprising the steps of:
    a) radiating a sample of said milk in a resonant cavity;
    b) measuring the amplitude of a scattering parameter of reflected microwave radiation caused by said sample of said milk in said resonant cavity; and
    c) determining said butterfat content of said milk as a function of said scattering parameter.

2. The method of measuring butterfat content in milk, as recited in claim 1, wherein said measuring step further comprises the step of measuring a frequency at which the reflected radiation is at a minimum.

3. The method of measuring butterfat content in milk, as recited in claim 1, further comprising the step of positioning said sample of said milk aligned with the E-field in said resonant cavity.

4. The method of measuring butterfat content in milk, as recited in claim 1, wherein said radiating step comprises the steps of:
 a) positioning a sample of said milk aligned with and at the center of a rectangular resonant cavity; and
 b) radiating said sample of said milk in said rectangular resonant cavity.

5. The method of measuring butterfat content in milk, as recited in claim 4, wherein said positioning step further comprises the step of providing a continuous flow of said sample of said milk through the center of said rectangular resonant cavity to accommodate measuring of said butterfat in a continuous stream of said samples of said milk.

6. The method of measuring butterfat content in milk, as recited in claim 5, further comprising the step of maintaining said continuous stream of samples of said milk at a constant temperature prior to said radiating step.

7. The method of measuring butterfat content in milk, as recited in claim 4, wherein said rectangular resonant cavity comprises:
 a) a first end having a short there across; and
 b) a second end having a radiator and an iris.

8. The method of measuring butterfat content in milk, as recited in claim 1, wherein:
 a) said radiating step comprises the steps of:
  i) positioning a sample of said milk aligned with and at the center of a first fork of a rectangular resonant cavity having a Y-configuration;
  ii) positioning a reference sample aligned with and at the center of a second fork of said rectangular resonant cavity having said Y-configuration;
  iii) radiating said sample of said milk in said first fork of said rectangular resonant cavity having said Y-configuration;
  iv) radiating said reference sample in said second fork of said rectangular resonant cavity having said Y-configuration; and
 b) said determining step further comprising the step of:
  i) normalizing said scattering parameter of said sample of said milk as measured at said first fork of said rectangular resonant cavity with a reference scattering parameter of said reference sample as measured at said second fork of said rectangular resonant cavity.

9. The method of measuring butterfat content in milk, as recited in claim 8, further comprising the step of activating a shutter in said rectangular resonant cavity having a Y-configuration to direct radiation between said first and second forks of said rectangular resonant cavity.

10. The method of measuring butterfat content in milk, as recited in claim 8, wherein said reference sample is water.

11. The method of measuring butterfat content in milk, as recited in claim 1, wherein said radiating step comprises the step of radiating a sample of said milk in a resonant cavity using microwaves in the X-band.

12. The method of measuring butterfat content in milk, as recited in claim 1, further comprising the steps of measuring a protein content of said milk, comprising the steps of:
 a) radiating said sample of said milk in a resonant cavity;
 b) measuring the amplitude of a scattering parameter of reflected microwave radiation caused by said sample of said milk in said resonant cavity; and
 c) determining said protein content of said milk as a function of said scattering parameter.

13. An apparatus for measuring butterfat content in milk using microwave absorption measurement techniques, comprising:
 a) a resonant cavity capable of resonating microwaves;
 b) a microwave energy source operably coupled to said resonant cavity to radiate said microwaves at said milk;
 c) a sample of said milk within said resonant cavity aligned with the E-field generated by said microwaves within said resonant cavity; and
 d) an analyzer operably coupled to said resonant cavity to measure the amplitude of a scattering parameter of reflected microwave radiation caused by said sample of said milk in said resonant cavity.

14. The apparatus for measuring butterfat content in milk using microwave absorption measurement techniques as recited in claim 13, wherein said microwave energy source and said analyzer are integrated into a network analyzer.

15. The apparatus for measuring butterfat content in milk using microwave absorption measurement techniques as recited in claim 13, wherein said resonance frequency of said resonant cavity is between 6 GHz and 21 GHz.

16. The apparatus for measuring butterfat content in milk using microwave absorption measurement techniques as recited in claim 13, wherein said resonant cavity is a rectangular resonant cavity.

17. The apparatus for measuring butterfat content in milk using microwave absorption measurement techniques as recited in claim 13, wherein said sample of said milk is a continuous flow of samples to accommodate measuring said butterfat in a continuous stream of said samples of said milk.

18. The apparatus for measuring butterfat content in milk using microwave absorption measurement techniques as recited in claim 13, wherein said resonant cavity is comprised of a rectangular resonant cavity having a Y-configuration comprised of:
 a) a first fork located at one branch of said Y-configuration rectangular resonant cavity for receiving said sample of said milk;
 b) a second fork located at another branch of said Y-configuration rectangular resonant cavity;
 c) a reference sample aligned within said second fork for use in differentially evaluating said sample of said milk from said reference sample; and
 d) a shutter operably coupled within said Y-configuration resonant cavity to alternatingly configure said resonant cavity to include said first fork having said sample of said milk and said second fork having said reference sample.

19. A resonant cavity to measure butterfat content in milk using microwave absorption measurement techniques, comprising:
 a) a metallic channel having first and second ends thereby defining the dimensions of said resonant cavity;
 b) an end plate electrically and physically coupled to said first end of said metallic channel to enclose said first end of said metallic channel in forming said resonant cavity;
 c) an iris electrically and physically coupled to said second end of said metallic channel to enclose said second end of said metallic channel in forming said resonant cavity, said iris having an aperture located therein to facilitate the entry of microwave radiation into said resonant cavity; and d) a sample tube centrally located within said resonant cavity for presenting said milk to said resonant cavity for subjection to said microwave absorption measurement techniques.

20. The resonant cavity to measure butterfat content in milk using microwave absorption measurement techniques, as recited in claim 19, wherein said sample tube is further coupled to a continuous flow of said milk to accommodate measuring of said butterfat in a continuous stream of said samples of said milk.

\* \* \* \* \*